United States Patent
Kutsch et al.

(10) Patent No.: US 6,325,624 B1
(45) Date of Patent: Dec. 4, 2001

(54) DEVICES AND METHODS FOR CONTINUOUS CONTACT AIR ABRASION DENTISTRY

(76) Inventors: V. Kim Kutsch, 1155 Twin Hills Dr., Jefferson, OR (US) 97352; Joe D. Deardon, 3445 Calavo Dr., Spring Valley, CA (US) 91978; Gregory S. Dollard, 1606 Hicks St., Oceanside, CA (US) 92109; Richard D. McEachern, 1360 Dexter Rd., Escondido, CA (US) 92029; Melvin B. Tamayo, 2118 Waterside Dr., Chula Vista, CA (US) 91913

(*) Notice: Subject to any disclaimer, the term of this patent is extended or adjusted under 35 U.S.C. 154(b) by 0 days.

(21) Appl. No.: 09/596,514

(22) Filed: Jun. 19, 2000

(51) Int. Cl.[7] .................................................. A61C 3/02
(52) U.S. Cl. ............................................. 433/88; 433/116
(58) Field of Search ...................................... 433/88, 116

(56) References Cited

U.S. PATENT DOCUMENTS

| | | |
|---|---|---|
| 2,696,049 | 12/1954 | Black . |
| 5,094,615 | * 3/1992 | Bailey ...................................... 433/88 |
| 5,547,376 | * 8/1996 | Harrel ....................................... 433/88 |
| 5,842,863 | * 12/1998 | Bruns et al. ........................ 433/88 X |
| 5,934,904 | 8/1999 | Elrod et al. .............................. 433/88 |
| 5,951,285 | * 9/1999 | Ho ........................................ 433/88 X |
| 5,957,760 | 9/1999 | LaSalle et al. ........................... 451/99 |

OTHER PUBLICATIONS

S Epstein, DDS, Analysis of airbrasive procedures in dental practice, JADA, vol. 43, Nov. 1951, pp578582.
HD White et al; Effects of air abrasive in prophylaxis, JADA, vol. 39, Aug., 1954, pp 155–163.
GE Meyers et al: The Airbrasive Technique A Report, British Dental Journal, Dec. 7, 1954, pp291–295.
Friedman, G et al Ultraconservative Resin Restorations "Watch and Wait" is not acceptable treatment, Dentistry Today, Jan., 2000, pp 67–.
Porth, R, Contact Air Abrasion, Dentistry Today, May 1999 pp 88–90.
Kutsch, VK, Contact cavity preparation using Welch Allyn's Kreativ Mach 6 air abrasion system, Jun. 2000 Dental Products Report pp98=99.
Dental Products Report, Apr. 2000 cover page advertisement.
Kreativ, Inc, Mach 5 and Mach 5 Plus Training Mnual and Reference Guide Jun. 1998 RevisionB.

* cited by examiner

*Primary Examiner*—Nicholas D. Lucchesi
(74) *Attorney, Agent, or Firm*—Lori M Friedman

(57) ABSTRACT

The present invention relates to a instrument for use in an air abrasion dental instrument that allows direct contact between a nozzle which delivers a stream of abrasive particles directly through a primary opening to a tooth surface. As the primary opening if the nozzles of this invention are in continuous close contact with a tooth surface, exhaust amounts of abrasive-laden fluid escape secondary openings at a direction lateral to the tooth surface. The invention also embodies removable nozzle covers having both primary and secondary openings that enable prior art nozzles to be easily converted to contact nozzles. Both the nozzles and removable nozzle covers of this invention define areas for dental restoration that remove a minimal amount of healthy tooth structure. The invention allows the comfort of air abrasion dentistry to the patient as well as both visual and tactile feedback to the dentist, the latter filling a long felt need of the practicing dental community.

24 Claims, 8 Drawing Sheets

COMPARATIVE FIG. 3b
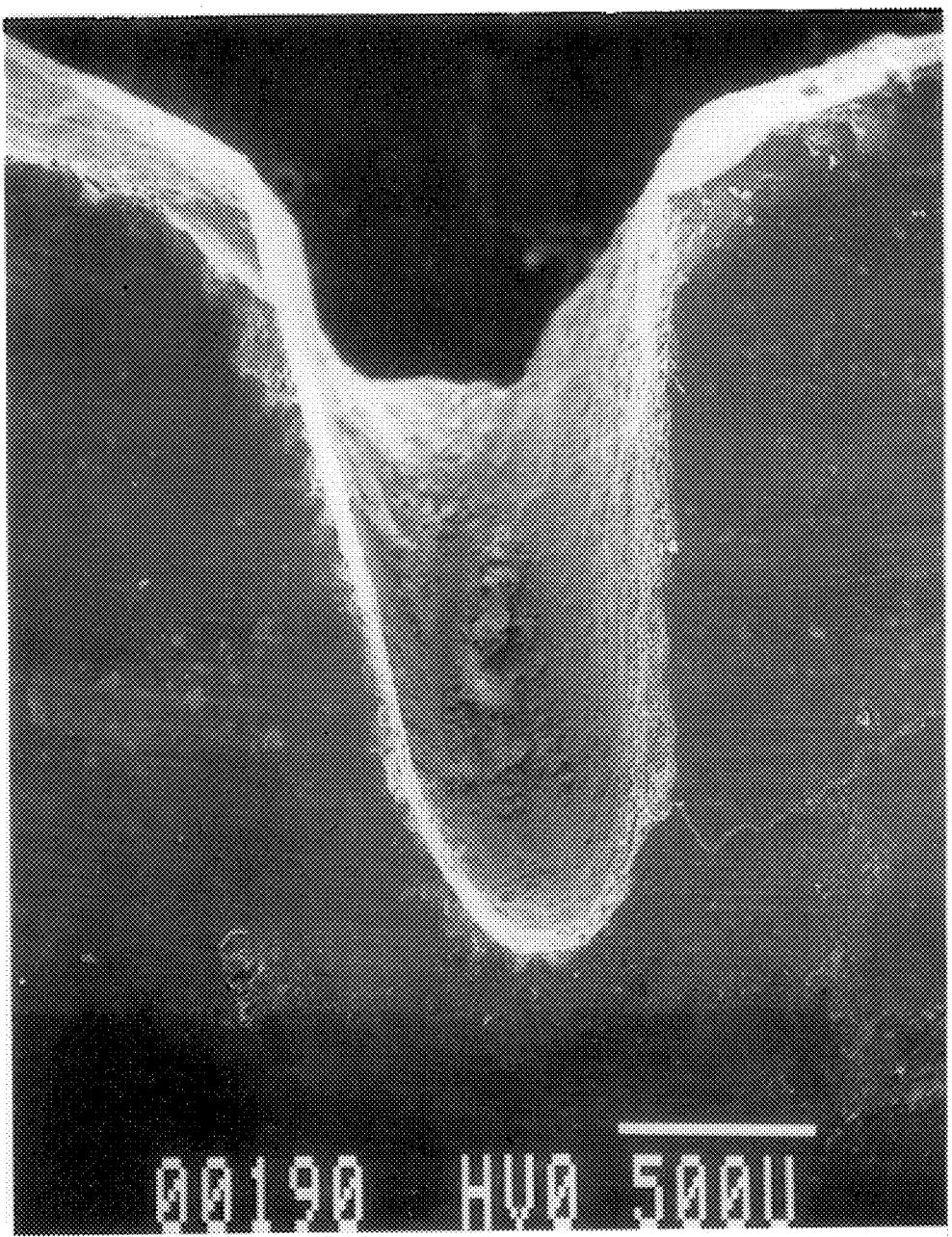
*PRIOR ART*

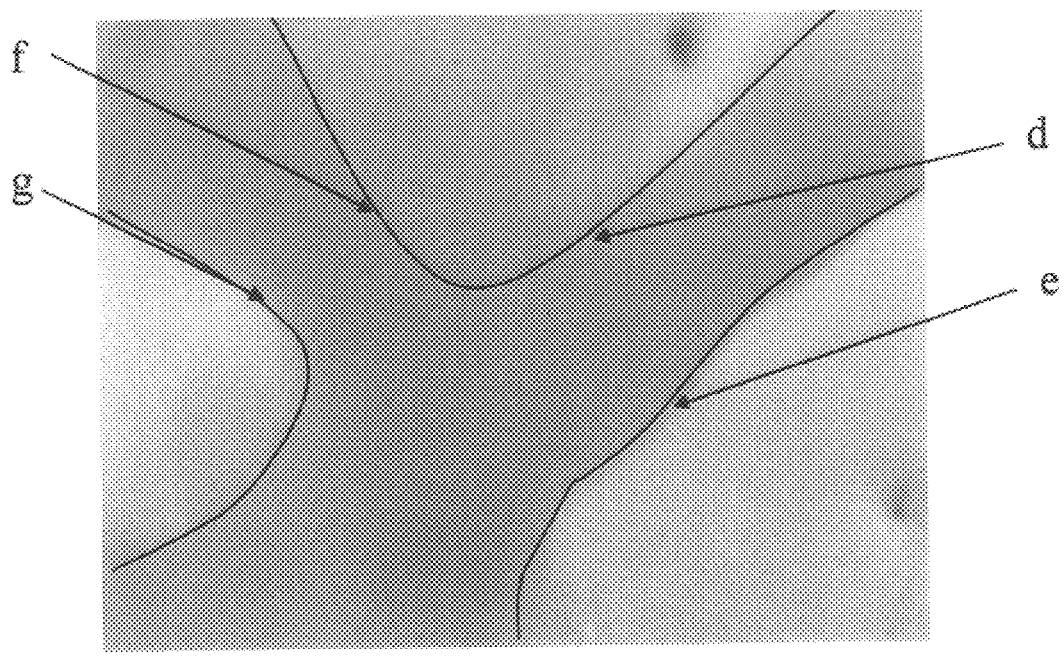
Comparative FIG 5A

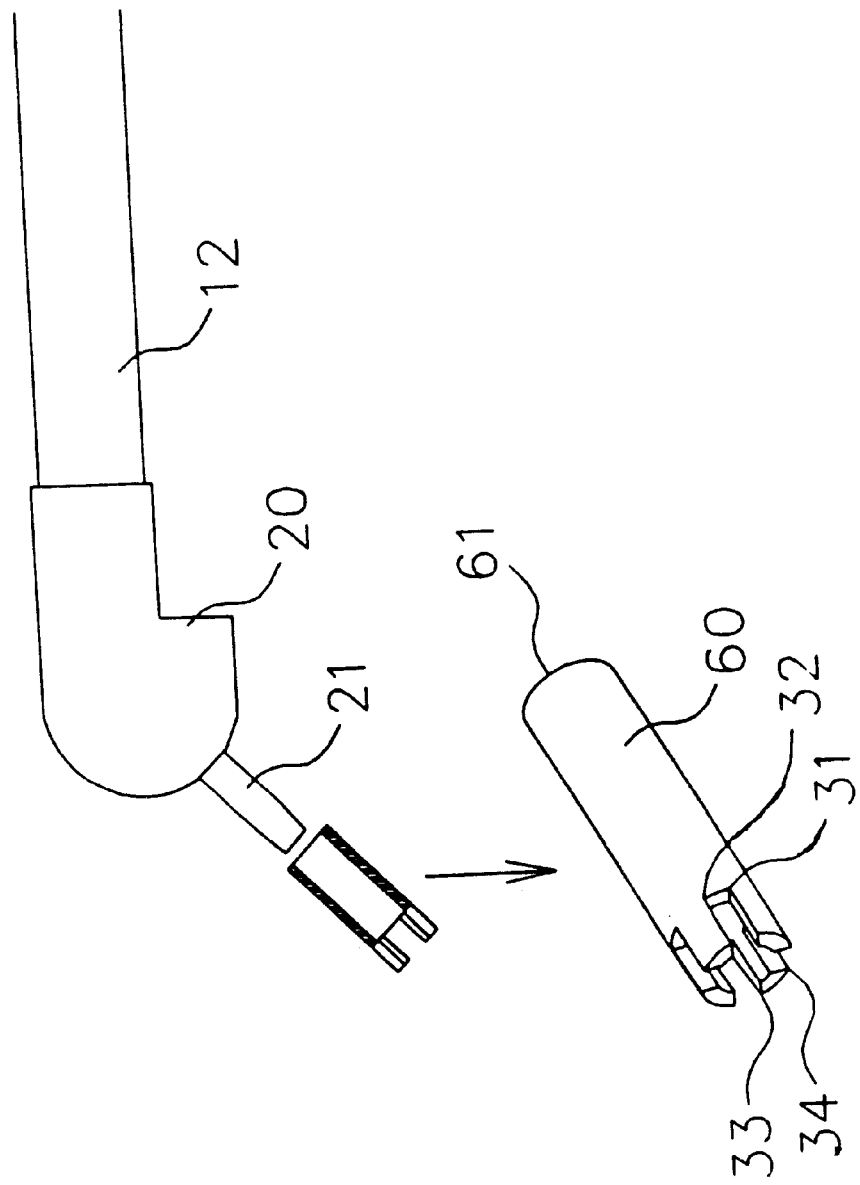

DEVICES AND METHODS FOR CONTINUOUS CONTACT AIR ABRASION DENTISTRY

BACKGROUND OF THE INVENTION

1. Field of the Invention

This invention relates to devices and methods for performing air abrasion dentistry. More specifically, the invention enables a dentist to receive both visual and tactile feedback while performing restorative dental procedures using certain types of air abrasion devices.

2. Background of the Prior Art

Air abrasion dental instruments employ a gas, usually air, which carries a stream of abrasive-laden fluid to tooth surfaces. Such a stream is directed onto a target tooth surface through a nozzle for removal of decay, preparing the teeth to receive fillings, prophylactic treatment, and the like. Air abrasion dental instruments provide advantages over conventional dental drills. These advantages include eliminating the heat, noise, and vibration produced by conventional high-speed drills. Also lessened is the need for anesthesia as well as the need to cool the drill with fluid. The general technique of treating teeth using such abrasives can be traced back to the 1950's and the work of Dr. Robert Black in U.S. Pat. No. 2,696,049.

There have been many improvements and added features in the decades following the issuance of the '049 patent in 1954. One feature of air abrasion dentistry that has remained the same for almost five decades is the fact that the nozzle which delivers abrasive particles must be held at a distance from the tooth surface. In the '049 patent, Dr. Black describes the distance the nozzle must be held from the tooth and emphasizes that better results occur when the distance is as short as possible. Although the distance is taught to be short, there must be some distance between the nozzle and the tooth. Thus, the dentist using traditional (prior art) air abrasion is experiencing a visual sensation only. This is unlike the visual and tactile feedback a dentist receives when using the tools of traditional, non-air abrasion dentistry.

Since the early days of air abrasion dentistry, many articles have been written by dentists desiring to enjoy the positive aspects of air abrasion dentistry but stymied by the fact that there is no tactile sensation to the dentist when using it.

Among these publications is a paper published in the *British Medical Journal* Dec. 7, 1954 by Dr. G. E. Myers entitled 'The Airbrasive Technique'. An article by Dr. S. Epstein in the *Journal of the American Dental Association* (JADA) November 1951 entitled 'Analysis of Airbrasive Procedures in Dental Practice' also expresses chagrin at the non-contact nature of air abrasion. Similar papers include 'Effects of Air Abrasive in Prophylaxis' by Dr. H. D. White et al in the August 1954 issue of JADA. A paper by Dr. R Goldstein et al entitled 'Air-Abrasive Technology: the New Role in Restorative Dentistry' appeared in JADA, May 1994. In this paper, Dr. Goldstein cites the lack of tactile guidance as a limitation of air abrasion dentistry.

The frustration of modem dentists with the lack of tactile feedback is a continuing problem. In the May, 1999 issue of Dentistry Today, Dr. Ronald Porth describes a technique entitles "Contact Air Abrasion". In this article, Porth explains how he uses traditional air abrasion equipment to achieve both tactile and visual feedback by moving a prior art nozzle in and out of contact with a tooth surface.

Porth's describes intermittent contact of a prior art nozzle with an irregular, non-flat tooth surface.

Porth describes various ways to move an ordinary air abrasion nozzle to allow venting while the nozzle is brought into intermittent contact with a tooth surface. Porth performed these motions not on flat tooth surfaces but on irregular molar surfaces with pits and fissures. Since they are movements in and out of contact, they are not the steady, continuous contact of a nozzle with a tooth surface taught by the instant invention. Prior to the present invention, constant contact of a prior art nozzle with a flat tooth surface terminated the cutting action of the abrasive-laden stream. There was also a likelihood that the nozzle will clog with abrasive particles or have bursts of particles when the process was restarted.

In the January 2000 issue of *Dentistry Today*, George Freedman comments on the lack of tactile feedback as being a negative point concerning air abrasion dentistry. The article is entitled "Ultraconservative Resin Restorations 'Watch and Wait' is Not Acceptable Treatment".

When using current air abrasive dental instruments such as the Kreativ Mach 5.0, the user is instructed to hold the nozzle of the handpiece at a distance from 5–10 mm from the surface of the tooth of interest. The Mach 5.0 dental instrument and procedures for its use are described in U.S. Pat. No. 5,934,904 entitled Dental Instrument and Processes and assigned to Kreativ, Inc. and herein incorporated by reference and made a part of this application.

In the April 2000 issue of *Dental Product Reports*, there is a product announcement for an air abrasion device designed to provide tactile feedback. In the June, 2000 issue of *Dental Product Reports* there is a detailed article by Dr. V. Kim Kutsch on the same air abrasion device. The device is covered by U.S. patent application Ser. No. 09/172327 entitled "Apparatus and Method for Particle Feeding by Pressure Regulation" which is assigned to Kreativ, Inc. Disclosed therein is a particle feeding system which alters particle flow to permit limited contact to a tooth surface using a prior art air abrasion nozzle.

Air abrasion dentistry requires air movement which combines with abrasive particles to create an abrasive-laden stream that cuts tooth structure. Until the present invention, dentists were required to aim the stream of abrasive-laden fluid towards the tooth surface of interest at a finite distance away from the tooth. If a prior art nozzle is placed in direct contact with a tooth surface, the nozzle's opening is partially or completely occluded, and airflow stops. The lack of air movement stops all cutting activity. However, the air abrasion device's powder feed mechanism continues to operate with reduced airflow volume. This often causes abrasive particles to build up in the device's feed line to the handpiece. This may result in an uncontrolled burst of abrasive particles when the orifice opens again, or it may clog the nozzle with particles. Dental handpieces equipped with nozzles that can successfully perform continuous contact air abrasion and methods for their use are subjects of this invention and are described herein.

SUMMARY OF THE INVENTION

The present invention is embodied in a dental instrument that is equipped with a handpiece ending in an elongated nozzle having a distal end that may be held in closed, continuous contact with a patient's teeth. The nozzle's distal end is configured so that when it is held in direct contact with a tooth surface, an abrasive-laden stream impinges upon the surface via a primary opening while a portion of the stream is vented laterally away from the tooth surface via at least one secondary opening.

The arrangement of primary and secondary openings in the nozzle of this invention is embodied in a handpiece that is part of a dental instrument. The handpiece of the dental instrument is connected to a source of pressurized abrasive-laden fluid which feeds a stream of abrasive-laden fluid through a central passageway defined in the nozzle for delivery of the stream to a tooth surface through the primary opening.

In this application, secondary openings include both vents and ports. Vents will refer to openings that are longer longitudinally than they are circumferentially. Similarly, in this invention ports will refer to rounded openings typically located within about one inch (25–30 mm) of the nozzle's distal end.

Secondary openings may be present in the nozzles of the present invention in a plurality of shapes or sizes. An opening in a nozzle that allows air to escape and relieve pressure from the target surface of a primary opening while the nozzle is held in continuous contact with the target surface in any manner is intended to be included in the scope of the present invention. The pressure relief provided by a secondary opening of a nozzle of this invention may be embodied by a variety of slits, slots, grooves, corrugations and the like in the nozzle.

The pressure relief afforded by the secondary openings of the nozzles of the present invention allows the dental practitioner to hold a handpiece nozzle's primary opening in direct contact with a tooth surface, providing him or her with both visual and tactile feedback. The dental instrument embodied by this invention will provide both the advantages of air abrasion dental treatment to the patient, such as less anxiety and pain, with the benefit of visual and tactile feedback to the dentist.

This invention also is embodied in removable nozzle covers with both primary and secondary openings that allow a prior art dental air abrasion nozzle to be used in direct contact with a tooth surface. The removable covers have both primary and secondary openings from which flow abrasive-laden fluid as described above. The descriptions provided for the contact nozzles of this invention also apply to the removable nozzle covers described herein.

The removable nozzle covers can be disposable. They are made of plastic or other light, inexpensive material. They are designed to easily slip over the tip of a non-contact (prior art) nozzle used to perform air abrasion dentistry. The shape and size of the vents or ports in the removable plastic nozzle covers of this invention are substantially the same as those of the non-removable nozzles described herein.

DESCRIPTION OF THE DRAWINGS

The preferred embodiments of this invention, illustrating all its features, will now be discussed in detail. These embodiments depict the novel and non-obvious dental instrument and process of this invention as shown in the accompanying drawings, which are for illustrative purposes only. This drawing includes the following figures (FIGS.), with like numerals indicating like parts:

Comparative FIG. 3b is cross-section photomicrograph of a cavity preparation made by a fissurotomy bur (prior art)

FIG. 6 depicts a removable nozzle cover with a primary opening and four vents that fits onto a prior art air abrasion nozzle.

DETAILED DESCRIPTION OF PREFERRED EMBODIMENTS

Figure 1:
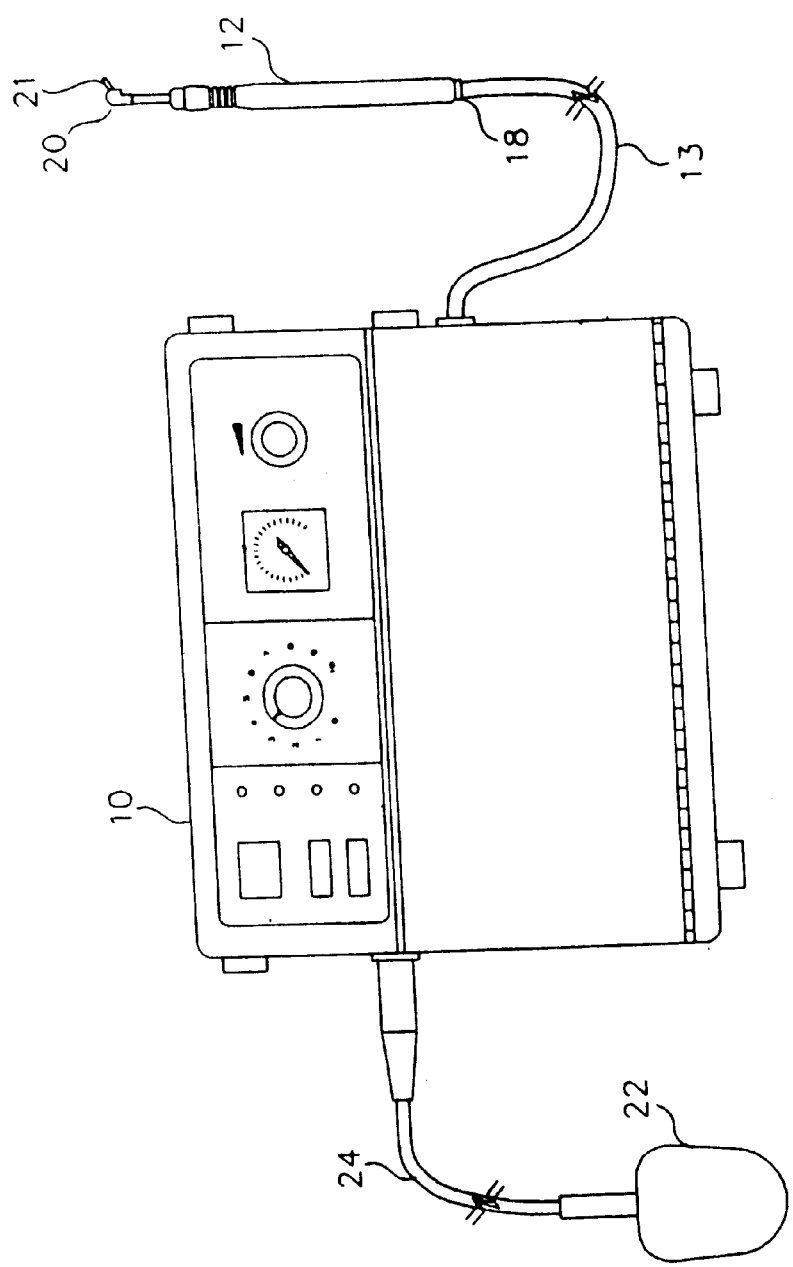
FIG. 1 is a pictorial diagram of an air abrasion dental instrument.

With reference to the drawings, and particularly to FIG. 1., devices and methods for performing contact air abrasion will be described. The dental instrument of this invention comprises a handpiece that includes a nozzle that enables the performance of air abrasion dentistry with direct contact of the nozzle to a tooth surface. A typical air abrasion instrument 10 in accordance with the present invention is illustrated generally in FIG. 1. An air abrasion handpiece 12 is connected by a hose 13 through the instrument 10 to a supply of abrasive particles (not shown) and a source of compressed air (not shown). The instrument 10 combines abrasive particles with the compressed air or other safe, non-toxic gas that may be found in a modern dental office. The mixture of abrasive particles and compressed air form a stream of abrasive-laden fluid that is directed through the hose 13 and the handpiece 12 through a nozzle head 20 ending in a nozzle 21 onto the surface of a tooth for removing material from its surface.

In this invention the nozzle 21 is an elongated nozzle having a distal end that defines a primary opening and a side wall that defines one or more secondary openings. A central passageway is defined in the nozzle, for delivering the pressurized stream of abrasive-laden fluid to the primary opening and the one or more secondary openings, for ejection therefrom.

A preferred gas used to carry abrasive to the tooth is air, although other safe, non-flammable gasses such as nitrogen or carbon dioxide, may be used. The source of air is generally an air compressor and reservoir of the type found in a dentist's office. An air compressor of this type provides pressurized air within the range of about 60–80 psig. FIG. 1 shows a foot-operated control 22 that is connected to the instrument and activates the instrument when depressed and deactivates it when released. When the system is activated, compressed air flows through it is regulated to the desired pressure. The abrasive particles are added to the compressed air to form the abrasive-laden fluid by internal mechanisms of the instrument 10. The instrument 10 controls the air pressure, the amount of abrasive particles added to the air stream, and the other operating characteristics of the dental instrument.

To use the device, the dentist places the distal end of the nozzle 21 in direct contact with a tooth surface whereupon the pressurized stream of abrasive-laden fluid impinges upon, and abrades, the surface via the primary opening, at least a portion of the pressurized stream then being redirected to the one or more secondary openings, for ejection from the nozzle in a direction lateral to the tooth surface.

The nozzles of this invention may be made of any metal that is able to withstand the high temperatures of sterilization used in dentistry. A preferred construction material for the nozzles of this invention is tungsten carbide. The nozzle may have its primary opening ranging in size from about 0.007 to about 0.048 inches (about 0.18 to about 1.2 mm) in diameter The nozzles used to perform the instant invention may be either standard nozzles or supersonic nozzles, the latter as described in U.S. Pat. No. 5,957,760 assigned to Kreativ, Inc. which is incorporated herein by reference and made a part of this application. Similarly, the removable nozzle covers will work with nozzles of any diameter and made of any material known and in use in the practice of dental air abrasion.

Figure 2B:
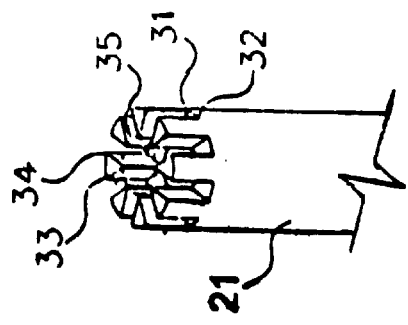
FIG. 2b depicts a contact nozzle with 8 vents.
Figure 2D:
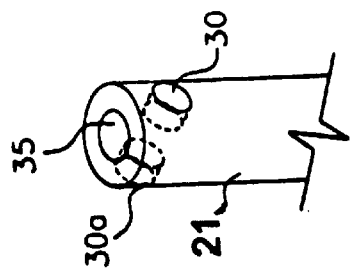
FIG. 2d depicts a nozzle with 2 ports.
Figure 2A:
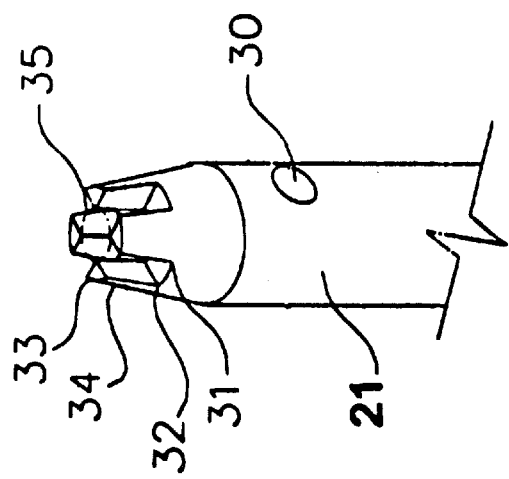
FIG. 2a depicts a contact nozzle of this invention with 4 vents and 2 ports.

FIG. 2a shows a nozzle 21 with ending in a primary opening 35 from which abrasive-laden fluid is emitted in direct contact with a tooth surface. FIG. 2a depicts a plurality of vents spaced circumferentially around the side wall. The nozzle depicted in FIG. 2a has four vents in a frusto-conical (beveled) portion of the nozzle's side wall in a castellated arrangement. The measurement between points 33 and 34 represent the width of a contact point of the nozzle to the tooth. In FIG. 2a, it is one of four contact points that touch the tooth surface while dentistry is performed on that tooth. The four contact points shown in FIG. 2a are pictured to be dimensionally equivalent, but they may not be. In FIG. 2a, the primary opening 35 is 0.018 inch (0.46 ) mm in diameter. The distance between contact points 33 and 34 is about 0.014 inch (0.36 mm). Since each of the four contact points of FIG. 2a are dimensionally equivalent, they each are about 0.014 inch (0.36 mm).

The dimensions of the contact points of the nozzles of this invention range from about 0.01 to about 0.02 inch (0.25 to 0.5 mm) depending on the size of the primary opening and on the number of secondary openings present in the nozzle.

In FIG. 2a, there are four vents. The distance between points 31 and 32 in FIG. 2a represents the width of a vent. As above, the width of the four vents of the nozzle pictured are dimensionally equivalent. A range for the width of the vents in an air abrasion nozzle with four vents may range from about 0.004 to 0.01 inch (0.1 to 0.254 mm). The width of the vents depends on the size of the nozzle's primary opening, the shape of nozzle (beveled or straight) and the total number of secondary vents present. A preferred width of the vent between points 31 and 32 and each of the three other vents pictured in FIG. 2a is about 0.006 inch (0.15 mm).

When being used to perform a dental operation, the nozzle's distal end is placed on a tooth surface by a dentist. Abrasive-laden fluid impacts a tooth surface through the primary opening 35 when the dentist sets the air abrasion unit to his specifications and depresses foot pedal 22. While abrasive-laden fluid is directed to a tooth from the primary opening 35, amounts of abrasive-laden fluid is laterally ejected through the secondary openings depicted in FIG. 2a. The lateral ejection of abrasive-laden fluid through the secondary openings prevents clogging of the pressurized stream of abrasive-laden fluid within the nozzle when the primary opening is fully occluded by a tooth surface.

Also depicted in FIG. 2a is a port 30 on one side of the nozzle 21. There is a second port (not shown) on the other side of nozzle 21 The number and dimensions of rounded secondary openings (ports) and longitudinal secondary openings (vents) may vary, but in all cases the combined volume of abrasive-laden fluid ejected from the secondary openings are at least equal to (and may oftentimes exceed) the volume of abrasive-laden fluid impacting the tooth at the primary opening of the nozzle.

FIG. 2b shows a nozzle with a primary opening 35 and eight (8) longitudinal secondary openings (vents) defining a non-beveled, castellated structure. The number of vents and the diameter of the primary opening will determine their width. The width of a nozzle contact point shown by 33 and 34 for the eight vent embodiment of the nozzle of this invention shown in FIG. 2b will typically range from about 0.004 inch (0.1 mm) to about 0.01 inch (0.254 mm). A preferred distance between nozzle contact points for the nozzle shown in FIG. 2b is about 0.006 inch (0.15 mm).

Figure 2C:
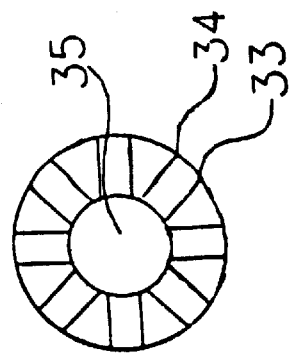
FIG. 2c depicts another view of a contact nozzle with 8 vents.

FIG. 2c depicts a schematic cross sectional view of the nozzle shown in FIG. 2b with eight vents. There are no rounded ports in this particular nozzle. The primary opening 35 of the nozzle is shown in the center of the eight nozzle contact points, whose width is represented by the distance between points 33 and 34. All of the abrasive-laden fluid directed to a tooth surface exits through the primary nozzle and secondary nozzles shown in FIG. 2c.

FIG. 2d shows a nozzle 21 with two (2) ports labeled 30 and 30a. The primary opening of this nozzle is 35 is the only point of contact between the nozzle and a tooth surface. The abrasive-laden fluid that is laterally directed away from the tooth surface in FIG. 2d is ejected through ports 30 and 30a.

The size of the ports-only contact nozzle depicted in FIG. 2d will generally depend on the diameter of the primary opening 35. The combined volumes of material flowing through the two ports 30 and 30 a are at least equal to the volume of primary opening 35.

The FIG. 2 series may be summarized as follows: Each nozzle has one primary opening 35. The secondary nozzles shown in FIG. 2a are four vents and two ports, for a total of six (6) secondary openings. FIGS. 2b and 2c illustrate a nozzle with only 8 vents. FIG. 2d shows a nozzle with only two ports. The nozzles of this invention each must have one primary opening. The number of secondary openings in any form, may be present in a range from one to ten.

Figure 3A:
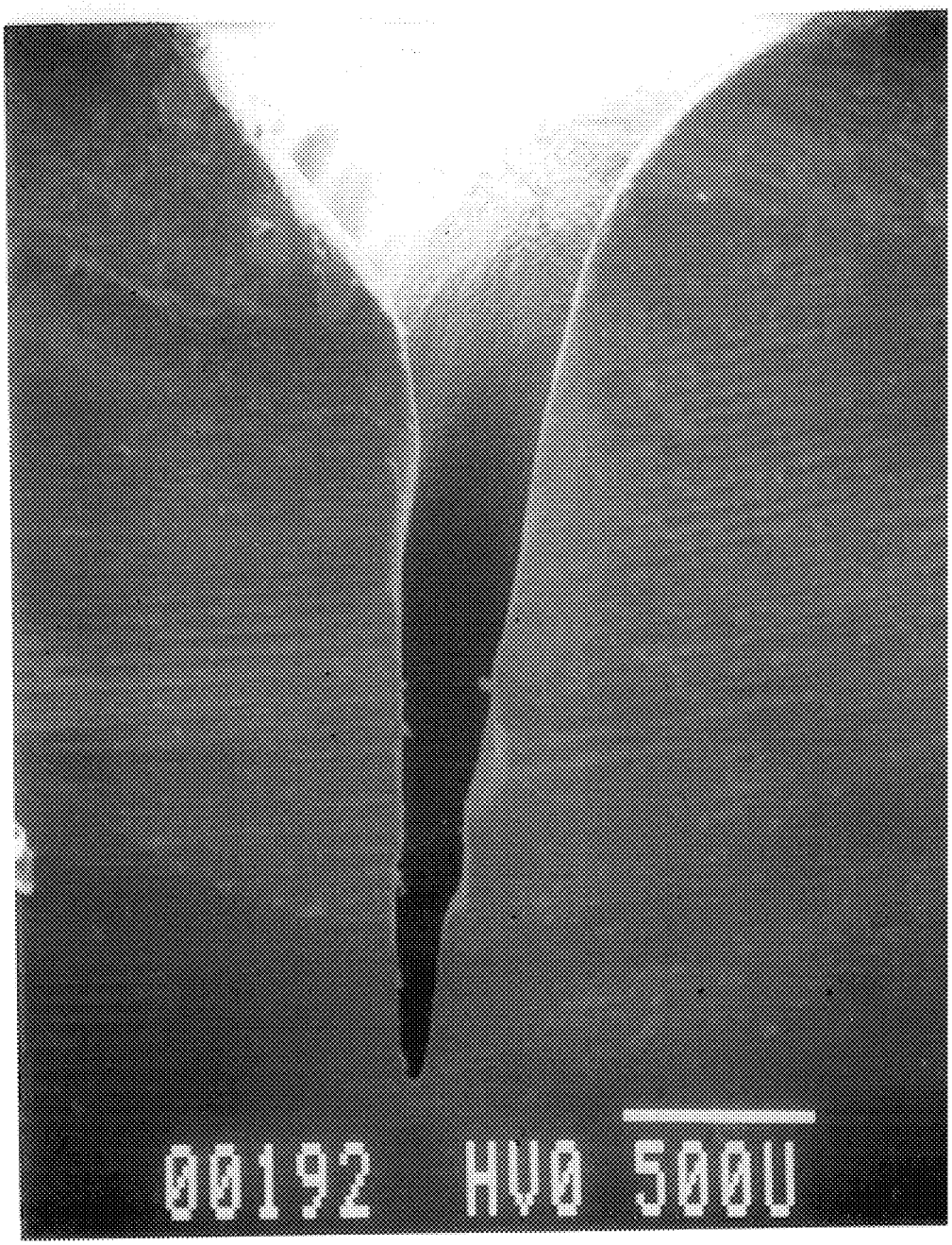
FIG. 3a is a cross-section photomicrograph of a crevasse cut into a tooth by a nozzle of this invention.

FIG. 3a is a photomicrograph of a cross-section of a crevasse cut into a tooth by a nozzle of this invention It depicts cross-section of a cavity preparation performed with a contact nozzle of the present invention with a primary opening of 0.011 inch (0.28 mm). The nozzle that made this cut has secondary openings of 4 vents and no ports.

Comparative FIG. 3b depicts a cross section of a cavity preparation performed with an SS White Fissurotomy bur. The shape and size of the bur are designed specifically for treating pit and fissure lesions. The bur allows a dentist to limit the bur tip to cut to just below the dentin/enamel junction (DEJ) and not further into the dentin, minimizing patient discomfort. The fissurotomy bur is designed to enlarge the fissure and eliminate small caries without excessively removing healthy enamel or dentin. This figure shows a tooth after the fissurotomy bur was used to perform an excisional biopsy of all the carious and suspect fissure areas of a tooth.

Both FIGS. 3a and Comparative FIG. 3b are photomicrographs that were made at 135× magnification. The difference in the size of the fissures made by a contact air abrasion nozzle of this invention (3a) and the fissurotomy bur (3b) is quite striking. As can be seen by the 500 micron scale in FIG. 3a and Comparative FIG. 3b, the fissure shown in FIG. 3a is much narrower than the fissure shown in FIG.

3b. Comparing FIG. 3a and Comparative FIG. 3b show that the tooth pictured in FIG. 3a has lost far less healthy enamel than the tooth pictured in FIG. 3b.

Figure 4:
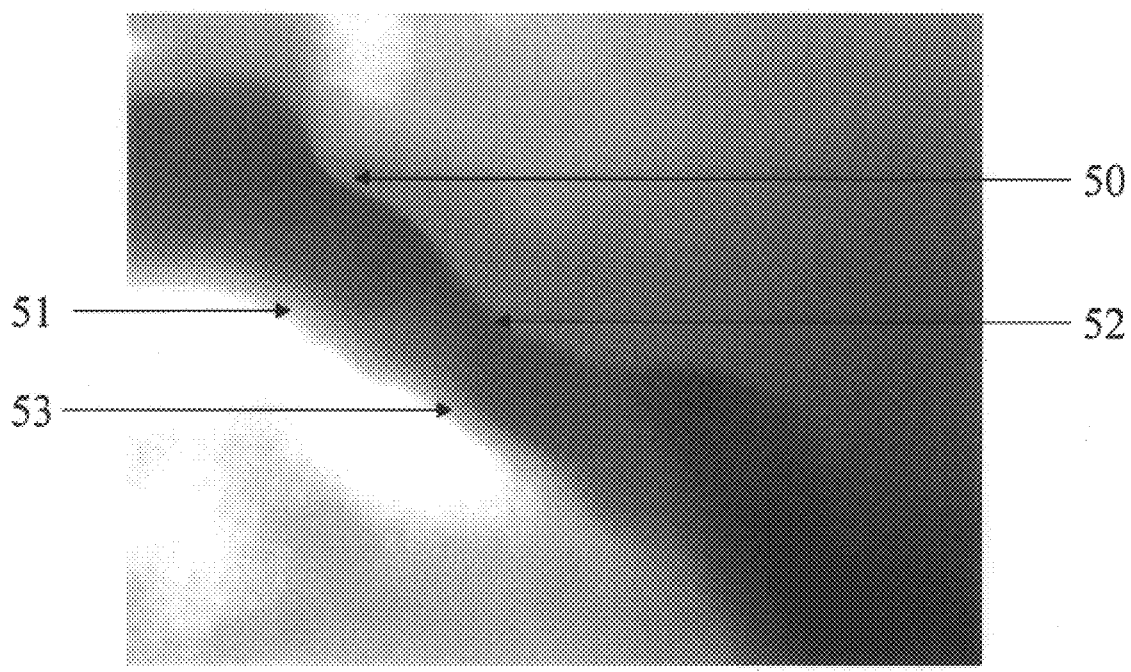
FIG. 4 is a photomicrograph of a crevasse-type cavity preparation in enamel by a nozzle tip of the present invention.
Figure 5:
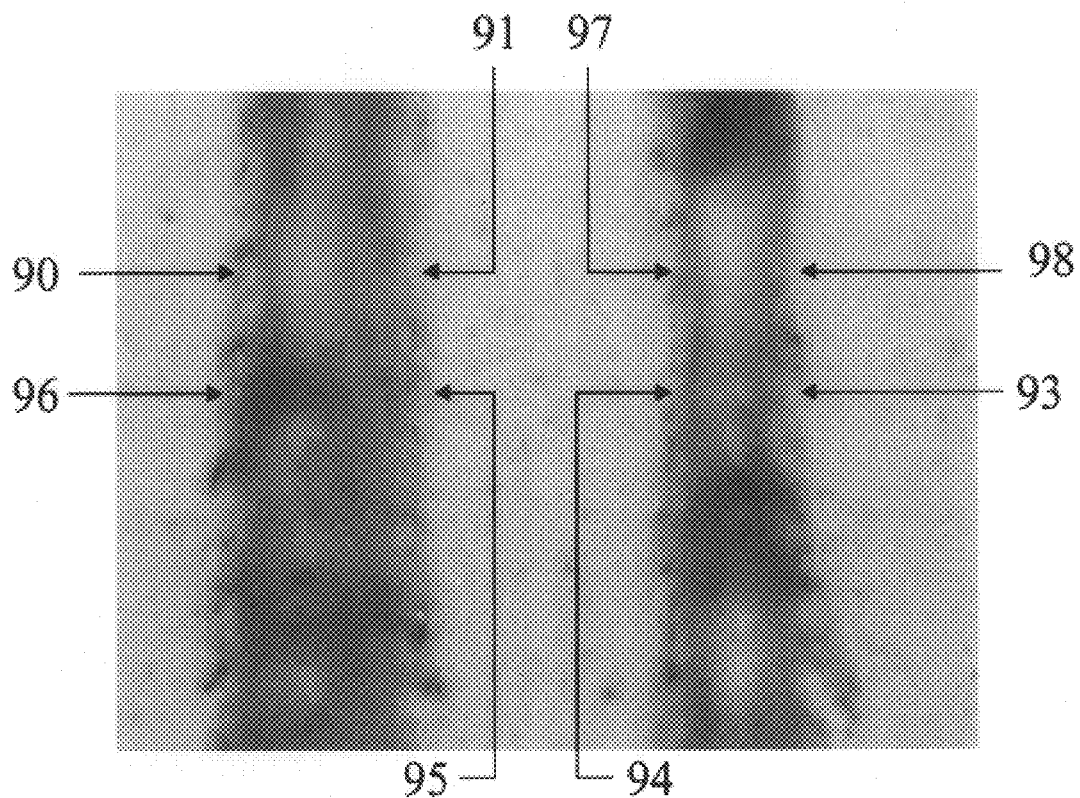
FIG. 5 shows a comparison of dental cuts made by a 0.0018 inch (0.46 mm) diameter nozzle in both prior art (left) and contact (right) done on a "Learn-a-Prep" square Comparative Figure A shows a wide valley that was cut in a tooth by a prior art nozzle in a tooth an 0.0018 inch (0.46 mm) diameter prior art nozzle.

FIGS. 4, 5 and Comparative Figure A are photomicrographs made using an Intel QX3 Computer Microscope. The instrument was used at 60×magnification to view various contact nozzles of the instant invention. The distances of the cuts made by both the contact and prior art air abrasion nozzles were measured using Matrox Inspector software version 1.7, from Matrox Electronic Systems, Ltd, (Dorval, PQ, Canada).

FIG. 4 shows a narrow, crevasse-type cavity preparation made in the enamel of a tooth. The crevasse was made with a nozzle depicted in FIG. 2a which is a nozzle with a primary opening with a diameter of 0.0018 inch (0.46 mm), four vents and 2 ports. The cut depicted in FIG. 4 has parallel axial walls and a near 90 degree cavosurface angle. Parallel axial walls are the walls on either side of the cut made by the nozzle of the present invention. In dentistry, the cavosurface angle is the angle in a prepared cavity formed by the junction of the wall of the cavity with the surface of the tooth. The angle is measured from the plane of the tooth.

The cut depicted in FIG. 4 between points 52 and 53 measures 0.0132 inch 0.34 mm). The cut between points 50 and 51 measures 0.0108 inch (0.27 mm). These cuts are quite narrow and precisely remove tooth debris while not removing much healthy tooth material.

A side-by-side comparison between the cuts made by the contact nozzles of this invention as compared with the prior art nozzles is also seen in FIG. 5. FIG. 5 compares cuts made in a square of "Learn-A-Prep" dental material. The cut on the left was made by a prior art 0.018 inch (0.46 mm) nozzle which made the cut in a tooth shown in Comparative Figure A. The cut on the right was made by the same 0.018 inch (0.46 mm) diameter contact air abrasion nozzle of this invention that cut the tooth pictured in FIG. 4 and that is shown in FIG. 2a.

The width of the cuts shown in FIG. 5 were measured using Matrox Inspector software version 1.7 are easily contrasted and compared The cut on the left, made with a prior art standard nozzle with a diameter of 0.018 inch (0.46 mm), was measured at two widths. The cut between points 90 and 91 measured 0.0188 inch (0.48 mm). The cut between points 95 and 96 measured 0.0284 inch (0.72 mm).

The cut made by a contact nozzle of this invention, with a 0.018 inch (0.46 mm) diameter primary opening, four vents and two ports, is shown on the right side of FIG. 5. Points on either side of the parallel axial walls of this cut were measured between points 97 and 98 as 0.0152 inch (0.39 mm), while the cut between points 93 and 94 measured 0.0184 inch (0.47 mm).

From FIG. 5, comparing instant and prior art nozzles of the same primary nozzle size (0.018 inch/0.46 mm), it is evident that the nozzle of this invention cuts at least 20% narrower than a comparable prior art, non-contact nozzle. The narrow, more precise cuts are beneficial to the dental health of the patient because there is less loss of healthy tissue. It also is beneficial for the dentist as he can use the instant nozzle to have both tactile and visual feedback while operating in direct contact with a tooth The cuts depicted in Comparative Figure A show a large amount of tooth structure that was cut by the non-contact, prior art nozzle. When the cavity preparations of FIG. 4 and Comparative Figure A are viewed side-by-side, the differences in the amount of tooth structure removed is noteworthy.

Comparative Figure A depicts a cut made into a tooth by a prior art, non-contact nozzle with an opening of 0.018 inch (0.46 mm) in diameter depicted herein has diverging axial walls. The cavosurface angle is much greater than 90 degrees. The cut made in a tooth between surface d and surface e measures 0.0308 inch (0.78 mm). The cut made between tooth surfaces f and g is 0.0192 inch (0.49 mm). The cavosurface angles depicted in Comparative Figure A are much greater than 90 degrees, and in fact are greater than 120 degrees The cavity walls depicted are not parallel but are in fact quite divergent.

FIG. 6 illustrates a removable nozzle cover 60 that comprises an elongated tubular body that includes a proximal end 61 sized to fit over the nozzle 21 of the handpiece 12 of a dental instrument, a distal end located opposite the proximal end from which abrasive-laden fluid is ejected through the primary opening 35, and a side wall located between the proximal end and the distal end. There is a central passageway defined within the tubular body which extends between the proximal end 61 and the distal end. A primary opening 35 is defined in the distal end of the tubular body that connects to the central passageway. There are a number of longitudinal secondary openings (vents) defined in the side wall of the tubular body in a castellated arrangement for connecting to the central passageway. The number of secondary openings in the removable nozzle cover 60 of this invention is related to the size of the nozzle 21 that it is to be fitted on. The plurality of secondary openings in the removable cover 60 are sized to prevent dogging of the pressurized stream of abrasive-laden fluid within the removable nozzle cover even when the primary opening 35 is fully occluded to a tooth surface.

The removable nozzle cover 60 is configured to be used to abrade a tooth surface by placing it over the nozzle 21 of a dental instrument. To perform contact air abrasion dentistry, the primary opening 35 of the removable nozzle cover 60 is placed in direct contact with a tooth surface, whereupon a pressurized stream of abrasive-laden fluid is directed through the central passageway to the primary opening 35 to impinge upon, and abrade, the tooth surface. At least a portion of the pressurized stream is simultaneously redirected to the one or more secondary openings, for ejection from the removable nozzle cover 60 in a direction lateral to the tooth surface. The combined cross-sectional areas of the plurality of secondary openings of the removable nozzle cover 60 is at least as large as the cross-sectional area of the primary opening 35. The distance between points 31 and 32 in FIG. 6 depicts the width of a longitudinal secondary opening of the removable nozzle cover.

The removable nozzle cover 60 as shown enables contact air abrasion dentistry to be performed by any air abrasion nozzle tip to which it is attached. One contact point of the removable cover is depicted by points 33 and 34. The distance between points 33 and 34 represent the width of a contact point of the nozzle to the tooth may range from about 0.01 inch to 0.02 inch (0.25 mm to 0.5 mm). A typical width of a contact point represented between 33 and 34 is about 0.014 inch (0.36 mm). The distance between points 31 and 32 in nozzle 21 depicts the width of a vent of the removable nozzle cover depicted.

Although FIG. 6 illustrates a removable nozzle cover with four vents, there may also be a number of ports. Just as in the case of the non-removable nozzles of this invention, the number and dimensions of secondary openings present as vents and/or ports may vary, but in all cases the combined volume of abrasive-laden fluid ejected from the secondary openings exceed are at least equal to the volume of abrasive-laden fluid impacting the tooth at the primary opening of the nozzle.

To use the nozzle cover 60 to practice contact air abrasion dentistry, a dentist will slip the cover 60 directly on to a nozzle 21. The nozzle cover 60 will be friction fitted to a non-removable nozzle. It will be resilient enough to be fitted on the nozzle 21 and will stay in place until removed by a user.

The materials from which the removable nozzles are made may be plastic or other suitable lightweight, inexpensive material. For purposes of this invention, any material that is inexpensive, machineable and strong enough to stay intact while being used in the application described herein may be used. Preferred materials are selected plastics from the group consisting of polyvinyl chloride (PVC), acetal resin, acrylonitrile butadiene styrene (ABS), polystyrene, and the like. Non-plastic materials that may be employed for the removable nozzle cover include Teflon and sintered carbide.

A comparison of the contact air abrasion nozzles of this invention and prior art nozzles in the Figures presented show that a much narrower cut may be made by a dentist using a contact air abrasion nozzle. In some cases, the dentist will hold the nozzle or nozzle cover of this invention slightly away from the contact surface. If the nozzle is held approximately 24 mm away from the target tooth surface, the cavity becomes more conical with cavosurface margin angles approaching 45 degrees. An advantage of the nozzles of this invention is that they may be held either in or out of contact with the target tooth surface.

It should be noted that the distal end of a nozzle 21 or removable nozzle cover 60 may be frusto-conical (beveled) or straight (non-beveled). Nozzles with beveled contact points generally afford the dentist a better view of the tooth of interest. Nozzles with non-beveled contact points will usually last longer. Both beveled and non-beveled nozzles are included in the scope of this invention.

The method of this invention allows the dental practitioner to 1) remove unwanted material from the tooth using air abrasive dentistry, thus allowing restoration without pain or the need for anaesthetic, 2) perform restorative dentistry while keeping the nozzle of the air abrasion instrument in direct contact with the tooth, 3) create narrow crevasse-like apertures while holding the nozzle in contact with the tooth, and finally 4) fill the cavity with a composite material that is esthetically pleasing and easily bonds to the remaining natural tooth structure.

In all instances, the nozzles of this invention have both primary and secondary openings. The combined cross-sectional areas of the one or more secondary openings is at least as large as the cross-sectional area of the primary opening. As a result, the combined volume of abrasive laden fluid that is ejected laterally through the secondary openings is at least equal to the volume of abrasive-laden fluid ejected to a tooth surface through the primary opening.

In practicing this methods of this invention, spent abrasive-laden fluid and other dental debris will exhaust through the nozzle's secondary openings. It is carried away from the patients mouth by an external suction device. High volume evacuation (HVE) is a standard feature of air abrasion dentistry. It may be provided with standard high volume evacuation means such as the Kreativ KleanAir® II, set on high speed at a distance about 8 inches (200 mm) from the patient's chin.

The abrasive particles used for contact air abrasion dentistry are selected from the group consisting of aluminum oxide, dolomite, urea, sodium bicarbonate and the like. A preferred abrasive material is Gamma Pure®, 27.5 micron aluminum oxide supplied by Kreativ. The particles, when the solid component of a abrasive-laden stream, are delivered to a tooth surface at a relatively high particle speed ranging from 110 to 160 meters per second. The particle flow rate ranges from 1 to 10 grams per minute. The stream is preferably at a pressure ranging from 15 to 120 psi.

EXAMPLES

As illustrated in the following Examples, the various parameters and conditions necessary for performing dental procedures are described using the contact nozzles of this invention. In air abrasion dentistry, it is generally recommended to use the lowest air pressure possible for a given procedure. It is also important to select a nozzle size suitable for the particular procedure. The larger the nozzle, the larger the cavity or hole it creates.

The following examples are meant for illustrative purposes only and are not intended to limit the instant invention in any manner whatsoever. A dentist who desires the use of air abrasion in his or her practice will be able to modify these procedures to individual needs, preferences, and patient comfort.

GENERAL INFORMATION ON NOZZLE SELECTION

For use with the Mach 5.0, Mach 5.0 Plus and subsequent models of Kreative® air abrasion equipment, Kreativ offers 0.011, 0.014, 0.018, 0.026, and 0.032 inch diameter nozzles. These are the sizes of the primary opening of the nozzle out of which a stream of abrasive-laden fluid is ejected. Supersonic handpiece assemblies are available in the same sizes up to 0.018 inch in diameter.

The use of a 0.018 inch diameter nozzle to remove large lesions and existing restorations is recommended. The use of a 0.014 inch diameter nozzle is recommended for most small lesions. A 0.011 inch diameter nozzle is best suited for very precise cutting such as diagnosis of occlusal pits and fissures, incipient Class II and Class III lesions or for placing fine retention in Class IV and Class V restorations.

The geometry of the cut made by the nozzle of the present invention is dependent on the size of its primary opening and the distance at which the nozzle is held from a tooth surface. For example, a 0.018"diameter nozzle held in contact with a tooth surface creates very conservative cavity preparations with near parallel axial walls as pictured in FIGS. 3a and 4. At a distance of 2–3 mm from a tooth surface, it produces a cavity that is more conical with cavosurface margin angles approaching 45 degrees.

Example 1

Procedure Protocols to Prepare Teeth for Class I, II, III, IV, V, and VI Restorations In the table below, all entries relate to procedures using the contact air abrasion nozzles of this invention. The air abrasion instrument used for these Examples was the Kreativ® Mach 5 instrument set in the Micro-Pulse mode. The abrasive particles used for all procedures is GammaPure® 27.5 micron aluminum oxide which is to be carried to the nozzle by air at a rate of 2–5 grams/minute.

TABLE 1

| Class | Particle Energy (psi) | Nozzle Diameter (inch) | Time (sec) |
|---|---|---|---|
| I | 40–80 | 0.014; 0.018 | 30–45 |
| II | 40–80 | 0.014; 0.018 | 45–60 |
| III | 40–80 | 0.011; 0.014; 0.018 | 20–30 |

TABLE 1-continued

| Class | Particle Energy (psi) | Nozzle Diameter (inch) | Time (sec) |
|---|---|---|---|
| IV | 40–80 | 0.011; 0.014; 0.018 | 30–45 |
| V | 15–40 | 0.011; 0.014 | 10–20 |
| VI | 40–80 | 0.011; 0.014 | 30–45 |

Notes for Table 1:
Use of a supersonic nozzle increases cutting efficiency and may be used for any class of restoration. The supersonic nozzle is not effective at particle energy below 50 psi.
Particle energy is noted in pounds per square inch (psi) and refers to the pressure at which abrasive particles are aimed at a target tooth surface.
Metric nozzle diameters listed in column three in Table 1 are 0.28, 0.36, and 0.46 mm.

Procedure

The 0.018 inch (0.46 mm) diameter contact nozzle, as pictured in FIG. 2a, is placed at a 90 degree angle relative to the plane of the tooth surface and in direct contact with the tooth surface to be treated. A 3-second burst of abrasive at a particle energy of 60 psi is used to trace out the grooves, pits, and fissures of the occlusal surface of any molar. The nozzle is held in one place until cavitation begins. When the cutting accelerates, the nozzle is moved slowly in the direction desired to extend the preparation. The flow of abrasive should be interrupted over areas of sound enamel, such as the isthmus separating the mesial and distal pits of mandibular molars and the oblique ridges of maxillary molars.

A caries detection dye such as MicroDetect (by Kreativ) should be used on all occlusal surfaces that are suspected of being carious. Thoroughly dry all tooth surfaces and grooves to be tested, apply MicroDetect for 10 (ten) seconds, rinse, dry, and gently abrade the stained (carious) areas. These steps should be repeated until no stained areas remain. It is important to use magnification when probing for small stained areas of decay.

After staining, the dentist observes and diagnoses cleaned pit and fissures for any remaining decay. Short, controlled bursts of abrasive-laden fluid should be used to remove all signs of decay in the fissures. Any exposed dentin must be noted for decay. If no decay is present, the tooth is ready for sealing.

If decay is present, the nozzle is held in contact with the tooth at a 60 psi particle energy setting for dentin and decay removal. As penetration proceeds deeper into the tooth, shorter bursts of abrasive-laden fluid at decreased pressure are used to ensure patient comfort. Procedures should be performed on the least affected areas first with short, controlled bursts of abrasive-laden fluid removing stained areas. Work is stopped frequently to observe any exposed dentin or decay into the dentin. If the patient feels discomfort, lower pressure and/or smaller nozzle tip sizes is attempted.

For Class V restorations and desensitization, particle energy of 40 psi is used to maximize comfort and ensure a more effective dentin seal. Class II and III restorations must have a matrix band and wedge in place before starting and to protect the gingiva and adjacent teeth. For interproximal caries, work starts away from the interproximal contact and slowly prepares towards it. The particle energy is reduced of necessary for patient comfort as the deeper recess is entered in the cavity preparation. When doing Class V or deep Class II restorations, the nozzle's distal end is moved away from the gingival sulcus or margin.

For all restorative dental procedures performed using the method of this invention, a nozzle of choice for the particular procedure is held in continuous, close contact with a tooth surface. A pressurizing stream of abrasive-laden fluid is delivered to the tooth surface throough the nozzle's primary opening with simultaneous lateral ejection of abrasive-laden fluid through the nozzle's secondary openings.

Example 2

Preparation of Teeth for Pit and Fissure Sealants

The air abrasion instrument (Kreativ Mach 5) was set at a particle energy of 40–60 psi, in the Micropulse Mode. The machine was set at a particle beam intensity of 2–4 grams of GammaPure® 27.5 micron alumina per minute. The contact nozzle diameter selected for this procedure was 0.011 inch (0.28 mm).

Procedure

Before preparation of the teeth for pit and fissure sealants, the procedures described above for using caries detection dye were performed. The stained areas were removed by moving the nozzle rapidly to avoid too much cutting in one area. The nozzle was kept in contact at the center of the pit and fissure and moved in a continuous sweeping motion to clean the pit and fissure. The procedure was continued with restorative materials such as pit and fissures sealants. These are resinous materials designed for application into the occlusal surfaces of posterior teeth to seal the surface irregularities and prevent entrance of oral fluids, food, and debris into the tooth. The time necessary for this preparation was 5–10 seconds per tooth.

Example 3

Removal of Spent Amalgam Dental Fillings

The air abrasion instrument (Kreativ Mach 5) was set at a particle energy of 80 psi, in the Powerpulse Mode. The machine was set at a particle beam intensity of 8–10 grams of GammaPure® 27.5 micron alumina per minute. The contact nozzle diameter selected for this procedure is 0.018 inch (0.46 mm).

Procedure

With the nozzle in contact with the target material, the nozzle was smoothly moved over the material to be removed with slow, steady motion. The nozzle was kept in contact with the tooth at all times using short, incremental cuts and continued until the removal is complete, including decay. The patient may experience a cold sensation when the particle beam first contacts vital dentin through the restorative material. Anesthetic is generally not required, as this sensation usually does not increase and often diminishes. After removal of amalgam and any decay, proceed with traditional etching and restoration. Notes: Some clinicians find it helpful to debulk amalgam restorations with a high speed handpiece and 330 carbide bur, being careful not to contact vital dentin, then switch to an air abrasion handpiece to remove the remaining amalgam and finish the cavity preparation. The above procedure is not effective removing large, deep Class II amalgam restorations. The procedure also will not replace acid etching for bonding.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A dental instrument for cutting tooth structure comprising:
    a source of a pressurized stream of abrasive-laden fluid; which is a dry mixture of abrasive particles and compressed air and
    a handpiece that includes an elongated nozzle having a distal end that defines a primary opening and a side wall that defines one or more secondary openings, wherein a central passageway is defined in the nozzle, for delivering the pressurized stream of abrasive-laden fluid to the primary opening and the one or more secondary openings, for ejection therefrom;
    wherein the instrument is configured to be used to abrade a tooth surface by placing the nozzle's distal end in direct contact with the surface, whereupon the pressurized stream of abrasive-laden fluid impinges upon, and cuts, the tooth surface via the primary opening, at least a portion of the pressurized stream then being redirected to the one or more secondary openings, for ejection from the nozzle in a direction lateral to the tooth surface.

2. The dental instrument of claim 1, wherein the side wall of the nozzle is generally cylindrical, having a longitudinal axis and a circumferential axis; and
    the one or more secondary openings defined in the side wall include a plurality of secondary openings spaced circumferentially around the side wall.

3. The dental instrument of claim 2, wherein the plurality of secondary openings are located in a portion of the side wall immediately adjacent to the distal end.

4. The dental instrument of claim 3 wherein the number of secondary openings ranges from one to ten.

5. The dental instrument of claim 3, wherein the plurality of secondary openings connect directly to the primary opening.

6. The dental instrument of claim 5, wherein the primary opening and the plurality of secondary openings define a castellated structure in the nozzle.

7. The dental instrument of claim 3, wherein the plurality of secondary openings are located in a frusto-conical portion of the side wall.

8. The dental instrument of claim 2, wherein the plurality of secondary openings are each longer longitudinally than they are circumferentially.

9. The dental instrument of claim 2, wherein the secondary openings are spaced from the nozzle's distal end.

10. The dental instrument of claim 1, wherein the one or more secondary openings are sized to prevent clogging of the pressurized stream of abrasive-laden fluid within the nozzle even when the primary opening is fully occluded.

11. The dental instrument of claim 1 wherein the nozzle is configured such that when the instrument is in use with the nozzle's distal end in direct contact with the tooth surface, the pressurized stream of abrasive-laden fluid abrades a portion of the surface that is substantially smaller than the cross-sectional size of the primary opening.

12. The dental instrument of claim 1, wherein the primary opening has a substantially circular cross-section with a diameter in the range of about 0.2 mm (0.008 inch) to about 1.25 mm (0.05 inch).

13. The dental instrument of claim 1, wherein the combined cross sectional areas of the one or more secondary openings is at least as large as the cross-sectional area of the primary opening.

14. A method for performing a dental procedure that cuts a tooth surface, comprising:
    providing a handpiece that includes an elongated nozzle having a distal end that defines a primary opening and a side wall that defines one or more secondary openings, wherein the handpiece further includes a central passageway that connects to the primary opening and the one or more secondary openings;
    delivering a dry, pressurized stream of abrasive-laden fluid to the central passageway of the handpiece, for delivery, in turn, to the primary opening and the one or more secondary openings and ejection therefrom; and
    holding the handpiece with the nozzle's distal end in direct contact with the tooth surface, such that the pressurized stream of abrasive-laden fluid impinges upon, and cuts the surface via the primary opening, at least a portion of the pressurized fluid then being redirected to the one or more secondary openings, for ejection from the nozzle in a direction lateral to the tooth surface.

15. The method of claim 14, wherein the one or more secondary openings defined in the side wall of the nozzle are sized such that holding the handpiece in such a way that the primary opening is fully occluded by the tooth surface causes the entire pressurized stream of abrasive-laden fluid to be ejected from the nozzle via the one or more secondary openings, without clogging.

16. The method of claim 14 wherein a user holding the handpiece in such a way that the primary opening of the nozzle is fully occluded by the tooth receives both tactile and visual feedback while working on the tooth.

17. A removable nozzle configured for use with a handpiece of a dental instrument of a kind that delivers a dry pressurized stream of abrasive-laden fluid to a base nozzle, for use in cutting a tooth surface, wherein the removable nozzle comprises:
    an elongated tubular body that includes
        a proximal end sized to fit over the base nozzle of the handpiece of the dental instrument,
        a distal end located opposite the proximal end, and
        a side wall located between the proximal end and the distal end;
    wherein a central passageway is defined within the tubular body, extending between the base end and the distal end;
    wherein a primary opening is defined in the distal end of the tubular body, for connecting to the central passageway;
    wherein one or more secondary openings are defined in the side wall of the tubular body, for connecting to the central passageway;
    and wherein the removable nozzle is configured to be used to cut a tooth surface by placing the removable nozzle over the base nozzle of the dental instrument, and by then placing distal end of the removable nozzle in direct contact with the tooth surface, whereupon the pressurized stream of abrasive-laden fluid is directed through the central passageway and the primary opening to impinge upon, and cut, the tooth surface, at least a portion of the pressurized stream then being redirected to the one or more secondary openings, for ejection from the removable nozzle in a direction lateral to the tooth surface.

18. The removable nozzle cover of claim 17, wherein the base end of the tubular body is sized to fit over the base nozzle of the handpiece of the dental instrument and to be secured thereto by a friction fit.

19. The removable nozzle cover of claim 17, wherein the tubular body is made of a material selected from the group consisting of polyvinyl chloride, acetal resin, acrylonitrile butadiene styrene, Teflon, and polystyrene.

20. The removable nozzle cover of claim 17, wherein the one or more secondary openings are sized to prevent clogging of the pressurized stream of abrasive-laden fluid within the removable nozzle even when the primary opening is fully occluded.

21. The removable nozzle cover of claim 17, wherein the removable nozzle is configured such that, when it is in use with its distal end in direct contact with the tooth surface, the pressurized stream of abrasive-laden fluid abrades a portion of the surface that is substantially smaller than the cross-sectional size of the primary opening.

22. The removable nozzle cover of claim 17, wherein the primary opening has a substantially circular cross-section with a diameter in the range of about 0.2 mm to about 1.25 mm.

23. The removable nozzle cover of claim 17, wherein the combined cross-sectional areas of the one or more secondary openings is at least as large as the cross-sectional area of the primary opening.

24. The removable nozzle cover of claim 17 wherein the number of secondary openings ranges from one to ten.

* * * * *

UNITED STATES PATENT AND TRADEMARK OFFICE
CERTIFICATE OF CORRECTION

PATENT NO. : 6,325,624 B1
DATED : December 4, 2001
INVENTOR(S) : Kutsch, V.K. et al.

It is certified that error appears in the above-identified patent and that said Letters Patent is hereby corrected as shown below:

<u>Title page,</u>
ABSTRACT, line 5, change "if" to -- of --

<u>Column 1,</u>
Line 62, change "entitles" to -- entitled --;
Line 66, change "Porth's" to -- Porth --;

<u>Column 8,</u>
Line 65, change "are" to -- or are --.

<u>Column 4,</u>
Line 12, change "Comparative Figure A" to -- Comparative Figure 5A --;

<u>Column 7,</u>
Lines 4, 34, 62 and 65, change "Comparative Figure A" to -- Comparative Figure 5A --;

<u>Column 8,</u>
Lines 1 and 8, change "change "Comparative Figure A" to -- Comparative Figure 5A --;

<u>Column 14,</u>
Line 64, change "nozzle cover" to -- nozzle --;

<u>Column 15,</u>
Lines 1, 5 and 10, change "nozzle cover" to -- nozzle --;

<u>Column 16,</u>
Lines 3, 7 and 10, change "nozzle cover" to -- nozzle --;

Signed and Sealed this

Thirtieth Day of April, 2002

*Attest:*

*Attesting Officer*

JAMES E. ROGAN
*Director of the United States Patent and Trademark Office*